United States Patent
Rempt

(10) Patent No.: US 7,304,474 B2
(45) Date of Patent: Dec. 4, 2007

(54) EDDY CURRENT INSPECTION DEVICE WITH ARRAYS OF MAGNETORESISTIVE SENSORS

(75) Inventor: Raymond Doak Rempt, Woodinville, WA (US)

(73) Assignee: The Boeing Company, Chicago, IL (US)

( * ) Notice: Subject to any disclaimer, the term of this patent is extended or adjusted under 35 U.S.C. 154(b) by 0 days.

(21) Appl. No.: 11/289,017

(22) Filed: Nov. 29, 2005

(65) Prior Publication Data

US 2007/0120560 A1 May 31, 2007

(51) Int. Cl.
G01R 33/09 (2006.01)
G01N 27/82 (2006.01)

(52) U.S. Cl. ............ 324/238; 324/235; 324/225; 324/252

(58) Field of Classification Search ........ 324/238, 324/235, 225, 252
See application file for complete search history.

(56) References Cited

U.S. PATENT DOCUMENTS

| | | | |
|---|---|---|---|
| 5,485,084 A | 1/1996 | Duncan et al. |
| 5,510,709 A | 4/1996 | Hurley et al. |
| 5,554,933 A | 9/1996 | Logue |
| 5,842,986 A | 12/1998 | Avrin et al. |
| 5,864,229 A | 1/1999 | Lund |
| 6,150,809 A | 11/2000 | Tiernan et al. |
| 6,504,363 B1 | 1/2003 | Dogaru et al. |
| 6,693,425 B2 | 2/2004 | Wache |
| 2003/0016131 A1 | 1/2003 | Nelson |
| 2003/0080735 A1 | 5/2003 | Wache |

OTHER PUBLICATIONS

William F. Arvin and Raymond D. Rempt; *Detection of Deep Flaws In Aluminum Structure With Magnetoresistive Sensors*; Review of Progress in Quantitative Nondestructive Evaluation; 1998; pp. 1039-1042, vol. 17; Plenum Press; New York.

William F. Arvin; *Magnetoresistive Eddy-Current Sensor For Detecting Deeply Buried Flaws*; Review of Progress in Quantitative Nondestructive Evaluation; 1996; pp. 1145-1150; vol. 15; Plenum Press; New York.

(Continued)

Primary Examiner—Reena Aurora
(74) Attorney, Agent, or Firm—Alston & Bird LLP

(57) ABSTRACT

There is provided an inspection device for the detection of flaws in a component. The inspection device comprises a magnetic field generator, a first array of magnetoresistive sensors and a second array of magnetoresistive sensors, in which the second array is substantially orthogonal to the first array. The signals generated by the first and second arrays are utilized by a processing element to determine a curl of the magnetic field signals effected by the eddy currents including the eddy currents encountering a flaw in the component. The curl of the magnetic field signals is then used to better illustrate the existence of the flaw and various parameters of the flaw. The magnetic field generator comprises a coil or linear arrays of conductors. The inspection device is preferably contained (1) within a hand-held housing or (2) mounted on any automated inspection platform, and advantageously comprises a display for illustration of the detected flaw.

28 Claims, 4 Drawing Sheets

OTHER PUBLICATIONS

Hiroshi Hoshikawa and Kiyoshi Koyama; *Uniform Eddy Current Probe With Little Disrupting Noise*; Review of Progress in Quantitative Nondestructive Evaluation; 1998; pp. 1059-1066; vol. 17, Plenum Press; New York.

Kiyoshi Koyama and Hiroshi Hoshikawa; *Basic Study Of A New ECT Probe Using Uniform Rotating Direction Eddy Current*; Review of Progress in Quantitative Nondestructive Evaluation; 1997; pp. 1067-1074; vol. 16; Plenum Press; New York.

William F. Arvin; *Eddy Current Measurements With Magneto-Resistive Sensors: Third-Layer Flaw Detection In A Wing-Splice Structure 25 mm Thick*; Nondestructive Evaluation of Aging Aircraft, Airports and Aerospace Hardware IV; Proceedings of SPIE; 2000; pp. 29-36; vol. 3994.

Buzz Wincheski and Min Namkung; *Deep Flaw Detection With Giant Magnetoresistive (GMR) Based Self-Nulling Probe*, date unknown.

J.P. Fulton, B. Wincheski, S. Nath and M. Namkung; *Mutual Inductance Problem For A System Consisting Of A Current Sheet And A Thin Metal Plate*, date unknown.

David Pappas; *Applications Of Magnetic Sensors*; National Institute of Standards and Technology, date unknown.

Buzz Wincheski; Min Namkung and John Simpson; *Magnetoresistive Sensor Based Rotating Probe System For Detection Of Deep Fatigue Cracks Under Airframe Fasteners*; The Fourth Joint NASA/FAA/Dod Conference on Aging Aircraft; 2000; pp. 1-10, 2000.

Buzz Wincheski and Min Namkung; *Electromagnetic Detection Of Fatigue Cracks Under Protruding Head Ferromagnetic Fasteners*; pp. 1-9, date unknown.

Teodor Dogaru, Carl H. Smith, Robert W. Schneider and Stuart T. Smith; *New Directions In Eddy Current Sensing*; http://www.sensorsmag.com/articles/0601/56/main.shtml, Mar. 5, 2004.

Teodor Dogaru and Stuart T. Smith; *Integrated Giant Magnetoresistive Transducer For Eddy Current Testing*; http://www.ndt.net/article/wendt00/papers/idn565/idn565.htm, Mar. 8, 2004.

Teodor Dogaru and Stuart T. Smith; *Novel eddy current probes for detection of deep cracks around fastener holes*; http://www.jcaa.us/AA_Conference_2001/Papers/2B_2.pdf.

EDDY CURRENT INSPECTION DEVICE WITH ARRAYS OF MAGNETORESISTIVE SENSORS

BACKGROUND OF THE INVENTION

1. Field of the Invention

Embodiments of the present invention are related to eddy current inspection devices, and more particularly, to inspection devices that include arrays of magnetoresistive sensors for measuring the curl of magnetic field signals effected by eddy currents encountering flaws.

2. Description of Related Art

Non-destructive evaluation (NDE) of a component to detect flaws or other features within the component may be performed by various techniques that include X-ray radiography, ultrasonics, acoustic emissions, and eddy currents. In particular, eddy current inspection devices are commonly used for NDE of electrically conductive components. Eddy current inspection devices typically use one or more excitation coils to generate an alternating magnetic field, which in turn induces eddy currents in the component.

The eddy currents induced in the component under inspection effect a magnetic field. However, when an eddy current encounters an internal flaw of the component, the eddy current flows around the flaw and changes the magnetic field. The pickup coil of the inspection device detects the resultant signals inductively. This detection provides information regarding the location and size of the flaw within the component.

These inductively detected signals are a time derivative of the actual magnetic field signals that are indicative of flaws. To improve the understandability or comprehendability of the measurements taken by the inspection device, a need exists to measure the current density giving rise to the magnetic field rather than the time derivative. Such measurements of current density would enable detection of flaws with improved visualization for the operator. Therefore, a need exists for an eddy current inspection device that accurately determines the current density resulting from the magnetic field signals effected by flaws.

BRIEF SUMMARY OF THE INVENTION

Embodiments of the present invention address the need for an inspection device that determines the current density of the magnetic field signals effected by flaws and/or features in a component being inspected. The inspection device determines the current density of the magnetic field signals by determining the curl of the magnetic field signals from measurements taken by two or more sensors included in the inspection device. An inspection device of an embodiment of the present invention generates a test magnetic field that induces eddy currents within a component under inspection. When the eddy currents encounter flaws in the component, the eddy currents are redirected around the flaw which changes the magnetic field signals effected by the eddy currents and, in turn, the current density associated with the magnetic field signals. By determining the curl of those magnetic field signals, rather than the time derivative of the magnetic field signals, the inspection device of one embodiment of the present invention allows improved visualization, such as with a display device, of the flaw by the operator and therefore affords improved detection of flaws as compared to devices that rely upon inductance measurements, since the operator can see how and where the currents are being redirected.

An inspection device of one embodiment includes a magnetic field generator that creates a test magnetic field directed into the component to induce eddy currents within the component. The magnetic field generator advantageously comprises a coil or a plurality of conductors defining a generally planar arrangement. The inspection device also includes at least two sensors that measure magnetic field signals effected by the eddy currents including those encountering the flaw in the component. The sensors generate at least two signals that are indicative of the measured magnetic field. Advantageously, the sensors comprise magnetoresistive sensors, such as anisotropic or giant magnetoresistive sensors. In addition, the sensors advantageously comprise two or more arrays of sensors and measure the magnetic field signals in at least two different directions that are substantially orthogonal. A processing element is also provided by the inspection device to receive and process the one or more signals to determine the curl of the magnetic field signals. These components of the inspection device are advantageously contained in a housing that may define a hand-held configuration for the inspection device.

In addition, an alternative inspection device includes a magnetic field generator to create a test magnetic field directed into the component to induce eddy currents within the component and includes at least two arrays of magnetoresistive sensors oriented in different directions. A first array of magnetoresistive sensors oriented in a first direction generates a first signal indicative of magnetic field signals effected by the eddy currents including those magnetic field signals effected by the eddy currents that encounter the flaws in the component and a second array of magnetoresistive sensors oriented in a second direction that is substantially orthogonal to the first direction, generates a second signal indicative of the magnetic field signals. A third array of magnetoresistive sensors oriented in the first direction may also be included to create a third signal indicative of magnetic field signals. The inspection device also includes a processing element that receives and processes the first and second signals to detect the flaw. These components of the inspection device are advantageously contained in a housing that may further define a display that illustrates the flaw in the component.

To inspect a component for flaws, the inspection device is positioned proximate a surface of the component. The inspection device creates a test magnetic field that is directed into the component to induce eddy currents within the component. Magnetic field signals are effected by the eddy currents including those encountering the flaws in the component. The inspection device detects the magnetic field signals to generate a signal indicative of the detected magnetic field signals and processes the signal to determine a curl of the magnetic field signals, which is proportional to the current density. Advantageously, the inspection device is scanned in a first direction relative to the component and indexed in a second direction relative to the component to determine the curl of the magnetic field signals. The inspection device may also display an image of the flaw based upon the curl of the magnetic field signals.

BRIEF DESCRIPTION OF THE SEVERAL VIEWS OF THE DRAWINGS

Figure 1:
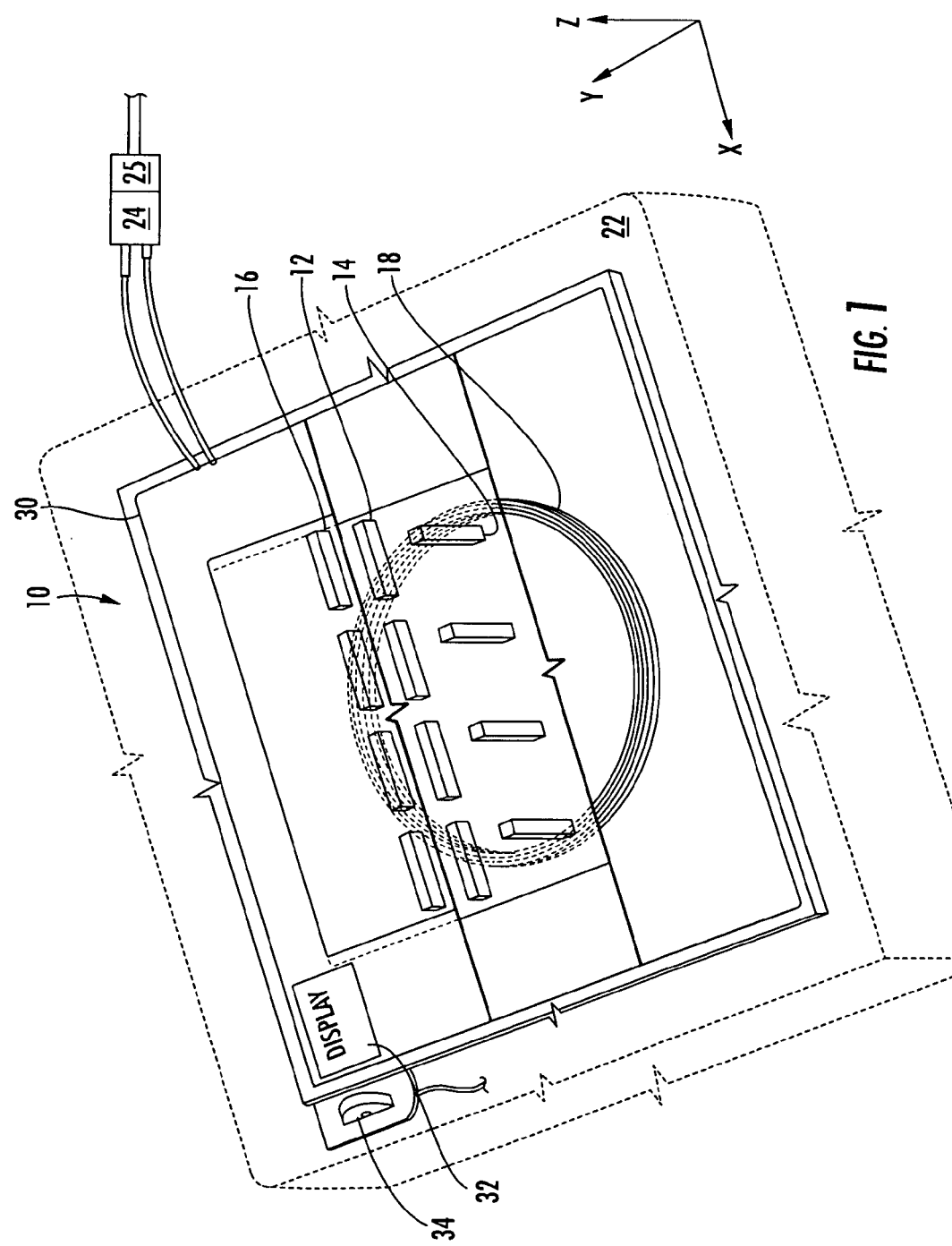
Figure 2:
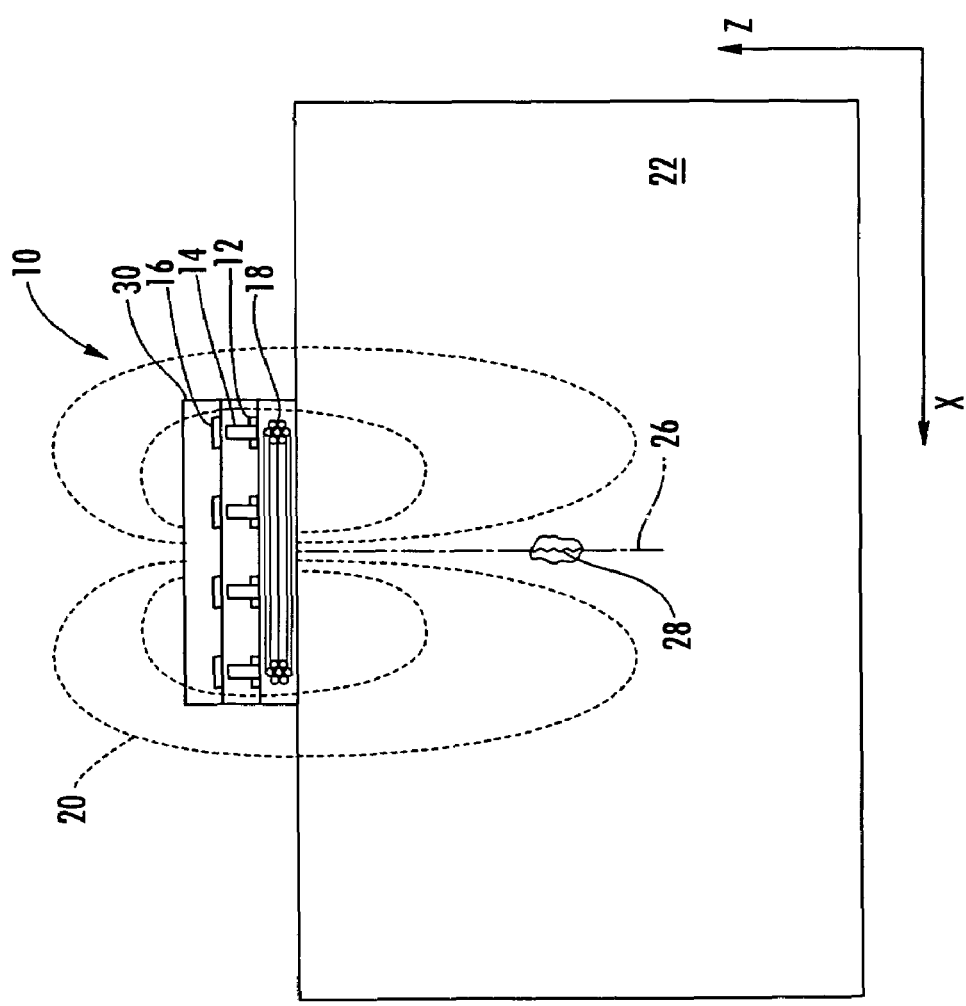
Figure 3:
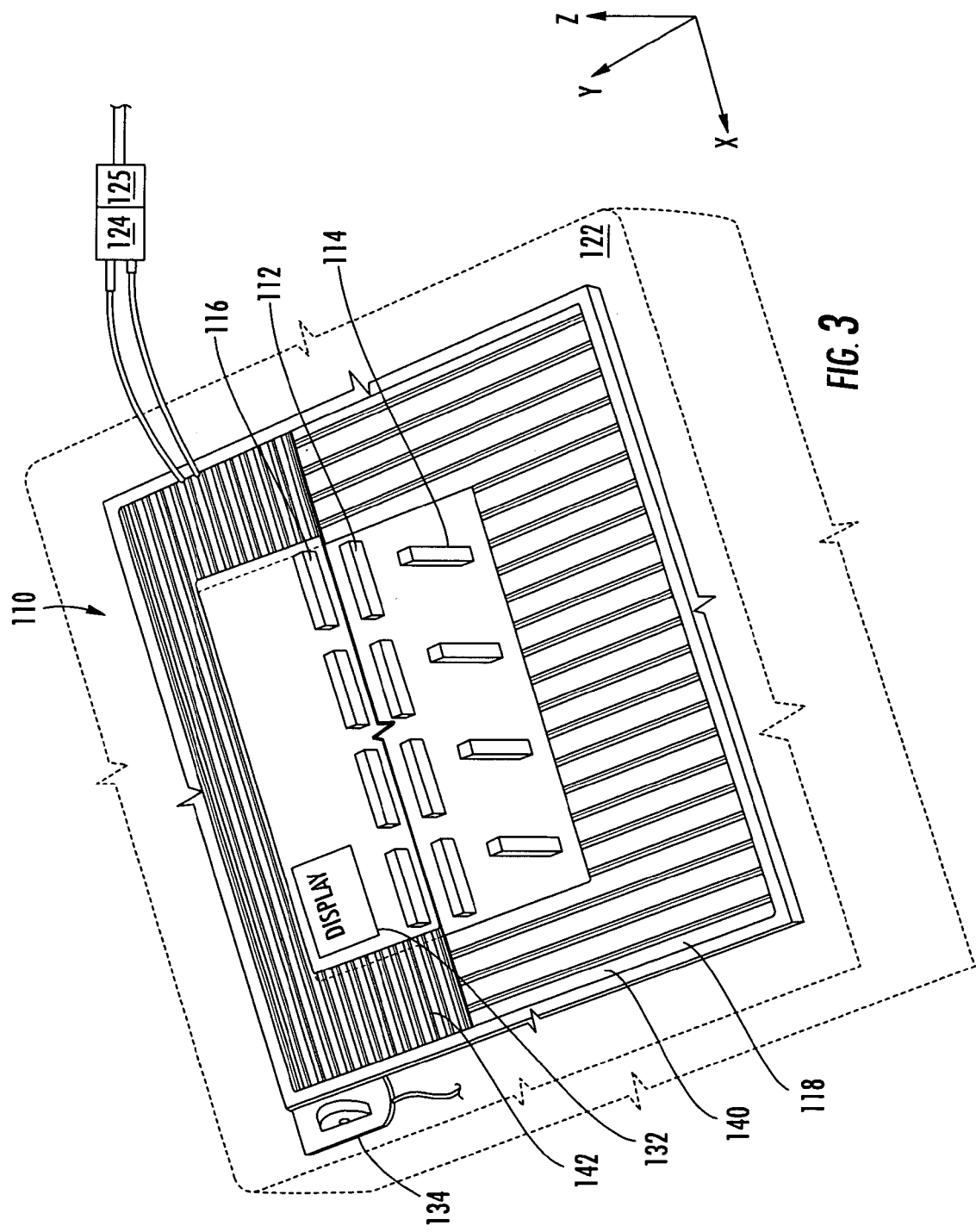
Figure 4:
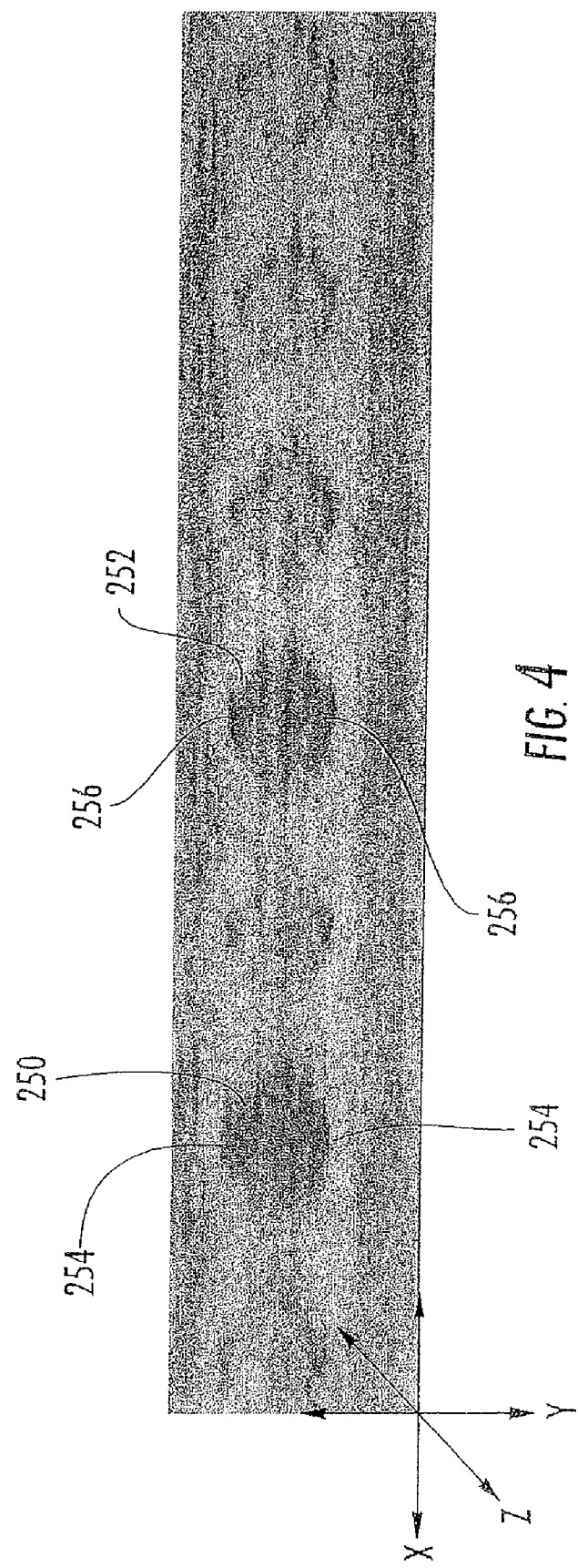

Having thus described the invention in general terms, reference will now be made to the accompanying drawings, which are not necessarily drawn to scale, and wherein:

FIG. 1 is a perspective view of an inspection device illustrating three arrays of magnetoresistive sensors and a magnetic field generator comprising a coil;

FIG. 2 is a descriptive side view of the inspection device of FIG. 1, illustrating the eddy currents induced in the component under inspection and a magnetic field signal effected by the eddy currents encountering a flaw;

FIG. 3 is a perspective view of an inspection device of a second embodiment of the present invention, illustrating three arrays of magnetoresistive sensors and a magnetic field generator comprising two pluralities of conductors defining a generally planar arrangement; and FIG. 4 is a top view of component under inspection as displayed by an inspection device of a third embodiment of the present invention, illustrating the detected slots in the second and fourth fastener holes from the left side.

DETAILED DESCRIPTION OF THE INVENTION

Two embodiments of the present invention will be described more fully with reference to the accompanying drawings. The invention may be embodied in many different forms and should not be construed as limited to only the embodiments described and shown. Like numbers refer to like elements throughout.

With reference to FIGS. 1-2, an inspection device 10 for the inspection of flaws, which may include undesirable defects or certain known or unknown features, in a component may be used, generally on-location ("in the field") or in a manufacturing or depot setting, to inspect any component suitable for eddy current inspection, such as an aircraft wing assembly, to list one non-limiting example. Such a component may include portions that are susceptible and that are not susceptible to induction. The inspection device 10 includes a first linear array of magnetoresistive sensors 12, a second linear array of magnetoresistive sensors 14, and a third linear array of magnetoresistive sensors 16. The inspection device 10 also includes a magnetic field generator 18 that creates a test magnetic field 20, as illustrated in FIG. 2, that induces eddy currents within the component 22 under inspection. As described more fully below, the orientation and position of the arrays of magnetoresistive sensors 12-16 enable the inspection device 10, using processing element 24, to determine the curl of the magnetic fields signals 26 effected by the eddy currents encountering a flaw 28 in the component. Various embodiments of the inspection device have magnetic field generators of differing shapes or orientations, sensors in alternative configurations, or additional elements to, for example, facilitate convenient handling of the device or to protect the sensors.

Referring again to FIG. 1, the inspection device 10 is shown as positioned on a component 22 under inspection. The inspection device 10 includes a magnetic field generator 18 that comprises a coil, as known to those skilled in the art. The coil defines a winding of electrically conductive material, such as copper to list one non-limiting example, which creates a test magnetic field 20 when current is provided to the coil by current source 25. As known in the art, the test magnetic field 20 induces, within the component 22, eddy currents that rotate about the axis of the coil generally in the x- and y-axes, and the eddy currents effect magnetic field signals 26, the density of which changes when the eddy currents encounter a flaw 28 within the component. The flaw 28 illustrated in FIG. 2 is generally oriented along the x- or y-axis, although flaws of any orientation may be detected by proper configuring of the inspection device 10. The magnetic field signal 26 of FIG. 2, which is effected by the eddy currents encountering the flaw, is illustrated along the z-axis; however, it should be appreciated that the magnetic field may extend along all three axes.

The inspection device 10 also includes at least two sensors that detect the magnetic field signals 26 effected by the eddy currents encountering the flaw 28 in the component 22. The sensors of the embodiments of the present invention illustrated in FIGS. 1-3 are arranged in linear arrays of sensors 12-16 that preferably define anisotropic magnetoresistive sensors; however, further embodiments of the present invention may define alternative sensors, such as giant magnetoresistive sensors to list one non-limiting example. The illustrated arrays comprise four sensors each; however, further embodiments of the present invention may comprise alternative numbers of sensors. The sensors of each array are preferably separated by an equal spacing, such as 0.1 inches, to list one non-limiting example. In addition, each array is preferably spaced from an adjacent array by a distance that is generally equivalent to the distance between sensors of each array, such as 0.1 inches, to list a non-limiting example.

The inspection device 10 includes a first array of magnetoresistive sensors 12 that is oriented in a first direction that is generally aligned with the x-axis of the inspection device, such that the first array of magnetoresistive sensors measures the x-axis component of the magnetic field signal 26 to generate a first signal indicative of the magnetic field signal effected by the eddy currents including those encountering the flaw 28 in the component. As discussed in more detail below, the inspection device 10 is preferably scanned in a first direction relative to the component, that is, along the y-axis of the inspection device. The processing element 24, which is preferably processing circuitry, such as a processor or other computing device to list non-limiting examples, is capable of determining the x-axis behavior of the magnetic field signals 26 by comparing the first signal provided by the first array of magnetoresistive sensors 12 at sequential, or random, y-axis positions of the inspection device.

The inspection device 10 also includes a second array of magnetoresistive sensors 14 that is oriented in a second direction that is generally orthogonal to the first direction. The individual magnetoresistive sensors are aligned with the z-axis of the inspection device, such that the second array of magnetoresistive sensors measures the z-axis component of the magnetic field signal 26 to generate a second signal indicative of the magnetic field signals effected by the eddy currents including those encountering the flaw 28 in the component. The first signal and second signal are received by the processing element 24. Therefore, the combination of the first and second arrays of magnetoresistive sensors 12 and 14 enables the processing element 24 to determine the x- and z-axis components of the magnetic field signals.

The inspection device 10 of FIGS. 1 and 2 further includes a third array of magnetoresistive sensors 16 that is oriented in the first direction that is generally aligned with the x-axis of the inspection device, such that the third array of magnetoresistive sensors measures the x-axis component of the magnetic field signal 26 to generate a third signal indicative of the magnetic field signals effected by the eddy currents. The third array of magnetoresistive sensors 16 is positioned at a different elevation in the z-direction, relative to the component under inspection, than the first and second arrays of magnetoresistive sensors. The third array is preferably positioned directly above the first array of magnetoresistive sensors 12 in the direction of the z-axis such that a comparison by the processing element 24 of the first and third signals provides z-axis information for the measured magnetic field signal 26. The second array of magnetoresistive sensors 14 of the illustrated embodiments is located along the z-axis midway between the first array of magnetoresistive sensors 12 and the third array of magnetoresistive 16 to facilitate comparison of the respective z-axis information. Some embodiments of the present invention include weighted variables when comparing the z-axis information provide by the first and third arrays and by the second array to compensate for differences in structure, location, or other parameters. Further embodiments of the present invention may comprise additional arrays of magnetoresistive sensors oriented in additional or alternative directions for the detection of the magnetic field signals.

The processing element 24 of the inspection device 10 utilizes the first, second, and/or third signals to determine a curl of the magnetic field signal 26. As known in the art, the curl is a property of a vector field that indicates the amount and direction of rotation of that vector. The curl of the magnetic field signal 26 is proportional to the current density of the magnetic field density at a particular point. The sensors of the inspections device 10 perform field sensing to measure the magnetic field signal rather than the inductive sensing (which measures the change in the number of flux lines passing through a given cross-section and is thus a time-derivative of the magnetic field signal) performed by standard eddy current inspection devices. Therefore, compared to the measurements made by standard inductive eddy current sensing devices, the inspection device 10 of embodiments of the present invention allows improved sensitivity, with a display device, of the detected deeply-lying flaw based upon the measured vector components of the magnetic field signal, and improved visualization by displaying current density indicative of flow interrupted by flaws. The curl is a vector product, such that determination of a particular component of the curl requires differentiation of the other two components of the field. The component of the curl that is typically of most interest is in the y-axis; therefore, the z-axis component and the x-axis component are determined and appropriate differences are calculated and subtracted from each other for calculation of the curl.

Referring now to FIG. 4, a visualization of current density, as displayed by an inspection device according to one embodiment of the present invention, is provided to illustrate the improved visualization provided by the present invention. The visualization of FIG. 4 is of a first component of 0.350 inch thick, in the z-axis, aluminum with fastener holes for 0.375 inch diameter fasteners covering a second component that is 0.395 inch thick, in the z-axis, and includes through-holes for the fasteners. The second component, which is below the first component along the z-axis, has slots in the second fastener hole 250 from the left and in the fourth fastener hole 252 from the left, at the 6 o'clock and 12 o'clock positions along the y-axis. The second hole has slots 254 that are 0.300 inch long in the y-axis, and the fourth hole has slots 256 that are 0.200 inch long in the y-axis. The visualization of FIG. 4 was created by scanning the component with a single sensor on two passes, with the sensor elevated by 1 millimeter during the second scan, relative to the first scan. The single sensor represents an array of sensors of the inspection device of the present invention, and the second scan at a different elevation represents a second array of sensors of the inspection device of the present invention. The example of FIG. 4 is provided only to illustrate the improved visualization of the present invention and is in no ways intended to limit the present invention to single sensor inspection devices or inspection devices that require multiple passes. The two resulting plots of the two scans were subtracted to determine the quantity dBy/dz from the relationship in which the curl Jx is approximately equal to dBy/dz minus dBz/dy. The quantity dBz/dy was computed from the data by subtracting adjacent points along the y-axis. The difference is visualized in the illustration of FIG. 4, which is proportional to the x-axis component of the current density. For the calculation of the curl for FIG. 4, the dBz/dy term is augmented by a factor of 0.9, to approximate the liftoff. The curl revealed in the two darkened fastener holes of the second fastener hole 250 from the left and the fourth fastener hole 252 indicate that the two fastener holes include flaws. The visualization of FIG. 4 enables an operator of the inspection device of the present invention to readily notice that flaws exist for the second and fourth holes from the left based upon the relative difference in shade or color when compared to the neighboring five holes. The visualization of FIG. 4 is provided for illustrative purposes only, as further embodiments provide visualization of components by alternative structures, such as with at least two sensors to list one non-limiting example, and/or by alternative processes, such as with a single scan to list another non-limiting example.

The inspection device 10 of FIGS. 1 and 2 may be contained within a housing 30 that may define a hand-held configuration such that an operator may conveniently grasp the inspection device and move the inspection device relative to the component under inspection. However, further embodiments of the present invention may comprise inspection devices that are for manual use but are not hand-held configurations or may be mounted on an automatic inspection platform. The inspection device 10 of FIGS. 1 and 2 also comprises a display 32 that preferably illustrates a plot or other image of the current density being proportional to the curl of the field measured by the inspection device or a graphical representation of the flaw, to list two non-limiting examples of use of the display. Alternatively, the inspection device may store the data for subsequent analysis or may transmit the data offboard for storage and/or analysis. The display 32 of FIG. 1 can be carried by the housing 30 of the inspection device 10; however, further embodiments of the present invention may mount the display on any automatic inspection platform or other surface.

The inspection device 10 of FIGS. 1 and 2 may also comprise a position sensor 34 that moves in concert with the first, second, and third arrays 12-16 of magnetoresistive sensors such that the position sensor provides position data of the inspection device during the inspection of the component 22. The position sensor 34 of the illustrated embodiment is an encoder wheel; however, further embodiments of the present invention may comprise alternative position sensors, such as an optical sensor, to list one non-limiting example particularly when the inspection device must be capable of moving in multiple directions, as described below. As shown in FIG. 1, the position sensor 34 is advantageously mounted to the housing 30 or other structure so that it moves in concert with the arrays 12-16 of magnetoresistive sensors. The position sensor 34 creates a signal that is advantageously processed, such as by the processing element, to provide position data of the inspection device 10 that may be correlated with the signals produced by the magnetoresistive sensors to accurately locate flaws that are detected by the pickup sensors. The position sensor 34 comprising an encoder wheel is preferably positioned to measure movement in the y-axis direction when the inspection device is scanned in a first direction relative to the component. Further embodiments of the inspection device may comprise alternative devices or methods for determining the position of the sensors when the inspection device is scanned in a first direction relative to the component and indexed in a second direction relative to the component or scanned with two dimensional motions with a trackball device or the like.

A second embodiment of the inspection device 110 is illustrated in FIG. 3, in which the magnetic field generator 118 comprises two pluralities of conductors defining a generally planar arrangement. U.S. patent application Ser. No. 10/923,519 filed Aug. 20, 2004 ("the '519 application"), assigned to the present assignee, discloses an inspection device having a magnetic field generator comprising conductors defining a generally planar arrangement, the disclosure of which is incorporated herein. FIG. 3 illustrates an inspection device 110 positioned on a component 122 under inspection. The inspection device 110 includes a first plurality of conductors 140 of the magnetic field generator disposed in a first plane and a second plurality of conductors 142 disposed in a second plane, such that the arrays are stacked relative to the component. As described in the '519 application, the two pluralities of conductors create a test magnetic field that induces eddy currents within the component that sweep 360 degrees in the x-y plane and that have a constant intensity throughout the entire 360 degree sweep. For inspection devices comprising magnetoresistive sensors or certain other types of sensors, the eddy currents and resulting magnetic field signals produced by at least one plurality of conductors defining a generally planar arrangement may afford improved performance relative to the eddy currents and resulting magnetic field signals produced by a coil; however, further embodiments of the present invention may provide optimal performance with any combination of sensors and magnetic field generators.

The inspection device 110 of FIG. 3 also includes a first linear array of magnetoresistive sensors 112, a second linear array of magnetoresistive sensors 114, and a third linear array of magnetoresistive sensors 116. Similar to the inspection device 10 of FIG. 1, the first, second, and third arrays of magnetoresistive sensors 112-116 detect the magnetic field signal effected by the eddy currents including those encountering the flaw in the component 122 to produce first, second, and third signals, respectively, that are received by the processing element 124. The processing element 124 processes the signals to determine the curl of the magnetic field signals to illustrate the current being redirected by flaws in the component.

Embodiments of the present invention also provide methods for performing an eddy current inspection of a component. To inspect a component 22 for flaws 28 as shown in FIG. 2, the inspection device 10 is positioned on a surface of the component. Advantageously, the housing of the inspection device 10 defines a hand-held embodiment that may be conveniently positioned on the component 22 by an operator in the field and conveniently moved along the component to inspect the desired regions of the component. For example, the component under inspection may be a portion of an aircraft, such as a wing portion, that may be field tested by the hand-held embodiment of the present invention by manually placing the inspection device upon the portion without disassembling the aircraft or other component under inspection. The magnetic field generator 18 of the inspection device 10 creates a test magnetic field 20 that is directed into the component to induce eddy currents within the component 22 so that magnetic field signals are effected by the eddy currents encountering the flaws in the component. At least two sensors, such as one array of magnetoresistive sensors, detects the magnetic field signals 26 to generate at least two signals that are indicative of the detected magnetic field signals and that is received by the processing element 24. Preferably, the first, second, and third arrays of magnetoresistive sensors 12-16 each produce signals that are received by the processing element 24. The processing element 24 processes the at least two signals to determine a curl of the magnetic field signals. The curl of the magnetic field signals 26 may be used to identify flaws in the component and to illustrate or otherwise quantify parameters of the flaw.

To inspect an area of the component 22, the inspection device 10 is moved relative to the component. Preferably, the inspection device is scanned in a first direction that is generally aligned with the y-axis of the inspection device. The inspection device may also be indexed in a second direction, which is different than the first direction, such as generally orthogonal to the first direction, to list one non-limiting example, in order to inspect a larger area of the component. Concurrent with the inspection of the component 22, the inspection device 10 preferably provides an image or numerical data on the display 32, in which the image or numerical data is based upon the determined curl of the magnetic field signals or the magnetic field signals themselves. Further embodiments of the inspection device comprise additional and alternative processes for inspecting a component.

Many modifications and other embodiments of the invention set forth herein will come to mind to one skilled in the art to which the invention pertains having the benefit of the teachings presented in the foregoing descriptions and the associated drawings. Therefore, it is to be understood that the invention is not to be limited to the specific embodiments disclosed and that modifications and other embodiments are intended to be included within the scope of the appended claims. Terms are used in a generic and descriptive sense and should not be used for purposes of limiting the scope of the invention except by reference to the claims and the prior art.

The invention claimed is:

1. An inspection device for the detection of a flaw in a component under inspection, comprising:
    a magnetic field generator to create a test magnetic field directed into the component to induce eddy currents within the component;
    at least first and third sensors that detect magnetic field signals effected by the eddy currents encountering the flaw in the component and received by the first and third sensors, wherein the first and third sensors generate at least two signals indicative of the detected magnetic field signals, wherein the first and third sensors are oriented in a common direction substantially parallel to a portion of the component under inspection, but offset from one another in a direction substantially orthogonal to the portion of the component under inspection;
    a second sensor oriented in a direction substantially orthogonal to the portion of the component under inspection, the second sensor configured to detect magnetic field signals effected by the eddy current encountering the flaw in the component and to generate a signal indicative of the detected magnetic field signals; and
    a processing element that receives and processes the signals from the first, second and third sensors to determine a curl of the magnetic field signals.

2. An inspection device according to claim 1 wherein the first and third sensors comprises at least two arrays of sensors.

3. An inspection device according to claim 1 wherein the second sensor extends between the first and second sensors in a direction substantially orthogonal thereto.

4. An inspection device according to claim 1 wherein the second sensor is generally positioned midway between the first and third sensors.

5. An inspection device according to claim 1 wherein the at least two sensors comprise magnetoresistive sensors.

6. An inspection device according to claim 5 wherein the magnetoresistive sensors comprise sensors from the group consisting of anisotropic magnetoresistive sensors and giant magnetoresistive sensors.

7. An inspection device according to claim 1, further comprising a housing that substantially encloses the magnetic field generator, the first, second and third sensors, and the processing element.

8. An inspection device according to claim 7, further comprising a display carried by the housing, wherein the display is in electrical communication with the processing element to illustrate the flaw in the component.

9. An inspection device according to claim 7 wherein the housing defines a hand-held configuration for the inspection device.

10. An inspection device according to claim 1 wherein the magnetic field generator comprises a coil.

11. An inspection device according to claim 1 wherein the magnetic field generator comprises at least one plurality of conductors defining a generally planar arrangement.

12. An inspection device according to claim 1 wherein the processing element is configured to determine information regarding the magnetic field signals in the direction orthogonal to the portion of the component under inspection based upon: (i) a comparison of the first and second signals and (ii) the third signals.

13. An inspection device for the detection of flaws in a component under inspection, comprising:
    a magnetic field generator to create a test magnetic field directed into the component to induce eddy currents within the component;
    first and third arrays of magnetoresistive sensors oriented in a first direction substantially parallel to a portion of the component under inspection, but offset from one another in a direction substantially orthogonal to the portion of the component under inspection, wherein the first and third arrays of magnetoresistive sensors generate first and third signals indicative of magnetic field signals effected by the eddy currents, including the eddy currents encountering the flaws in the component, and received by the first and third arrays of magnetoresistive sensors;
    a second array of magnetoresistive sensors oriented in a second direction that is substantially orthogonal to the first direction and substantially orthogonal to the portion of the component under inspection, wherein the second array of magnetoresistive sensors generate a second signal indicative of magnetic field signals effected by the eddy currents, including the eddy currents encountering the flaws in the component, and received by the second array of magnetoresistive sensors; and
    a processing element that receives and processes the first, second and third signals to detect the flaw.

14. An inspection device according to claim 13, wherein the second array of magnetoresistive sensors extends between the first and third arrays of magnetoresistive sensors in a direction substantially orthogonal thereto.

15. An inspection device according to claim 14 wherein the processing element processes the first, second, and third signals to determine a curl of the magnetic field signals.

16. An inspection device according to claim 14 wherein the first, second, and third arrays of magnetoresistive sensors comprise an equivalent number of magnetoresistive sensors.

17. An inspection device according to claim 14 wherein the magnetoresistive sensors comprise sensors from the group consisting of anisotropic magnetoresistive sensors and giant magnetoresistive sensors.

18. An inspection device according to claim 14, further comprising a housing that substantially encloses the magnetic field generator; the first, second, and third arrays of magnetoresistive sensors; and the processing element.

19. An inspection device according to claim 18, further comprising a display carried by the housing, wherein the display is in electrical communication with the processing element to illustrate the flaw in the component.

20. An inspection device according to claim 13 wherein the second array of magnetoresistive sensors is positioned, midway between the first and third arrays of magnetoresistive sensors.

21. A method of inspecting a component for one or more flaws, the method comprising:
    providing an inspection device comprising first, second and third sensors, wherein the first and third sensors are oriented in a common direction substantially parallel to a portion of the component, but offset from one another in a direction substantially orthogonal to the portion of the component, and wherein the second sensor is oriented in a direction substantially orthogonal to the portion of the component;
    creating a test magnetic field directed into the component to induce eddy currents within the component so that magnetic field signals are effected by the eddy currents, including the eddy currents encountering the flaws in the component;
    detecting magnetic field signals effected by the eddy currents including the eddy currents encountering a flaw in the component;
    generating first, second and third signals with the first, second and third sensors, respectively, indicative of the detected magnetic field signals; and
    processing the first, second and third signals to determine a curl of the magnetic field signals.

22. A method according to claim 21, further comprising scanning the inspection device in a first direction relative to the component and indexing the inspection device in a second direction, which is different than the first direction, relative to the component.

23. A method according to claim 21, further comprising displaying an image of the flaw based upon the determined curl of the magnetic field signals.

24. A method according to claim 21 wherein measuring magnetic field signals comprises measuring the magnetic field signals in at least two directions that are substantially orthogonal.

25. An inspection device according to claim 13 wherein the processing element is configured to determine information regarding the magnetic field signals in the direction orthogonal to the portion of the component under inspection based upon: (i) a comparison of the first and second signals and (ii) the third signals.

26. A method according to claim 21 wherein providing the inspection device comprises providing the inspection device in which the second sensor extends between the first and second sensors in a direction substantially orthogonal thereto.

27. A method according to claim 21 wherein providing the inspection device comprises providing the inspection device in which the second sensor is generally positioned midway between the first and third sensors.

28. A method according to claim 21 wherein processing the first, second and third signals comprises determining information regarding the magnetic field signals in the direction orthogonal to the portion of the component based upon: (i) a comparison of the first and second signals and (ii) the third signals.

* * * * *